US011350813B2

(12) United States Patent
Nishio

(10) Patent No.: US 11,350,813 B2
(45) Date of Patent: Jun. 7, 2022

(54) ENDOSCOPE SYSTEM

(71) Applicant: OLYMPUS CORPORATION, Tokyo (JP)

(72) Inventor: Masahiro Nishio, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 590 days.

(21) Appl. No.: 16/218,659

(22) Filed: Dec. 13, 2018

(65) Prior Publication Data

US 2019/0110663 A1 Apr. 18, 2019

Related U.S. Application Data

(63) Continuation of application No. PCT/JP2016/067810, filed on Jun. 15, 2016.

(51) Int. Cl.
*A61B 1/00* (2006.01)
*A61B 1/06* (2006.01)
*A61B 1/05* (2006.01)

(52) U.S. Cl.
CPC ...... *A61B 1/00096* (2013.01); *A61B 1/00006* (2013.01); *A61B 1/00163* (2013.01);
(Continued)

(58) Field of Classification Search
CPC ... A61B 1/00096; A61B 1/06; A61B 1/00006; A61B 1/00163; A61B 1/05; A61B 1/0676; A61B 1/00009; H05B 45/10; H05B 45/18
See application file for complete search history.

(56) References Cited

U.S. PATENT DOCUMENTS

2007/0112247 A1* 5/2007 Hirata ............... A61B 1/0684
600/101
2010/0080016 A1* 4/2010 Fukui ................. G02B 6/32
362/574
(Continued)

FOREIGN PATENT DOCUMENTS

JP 07241270 A * 9/1995
JP 2005-6854 A 1/2005
(Continued)

OTHER PUBLICATIONS

International Search Report dated Septembers, 2016 received in International Application No. PCT/JP2016/067810.
(Continued)

*Primary Examiner* — Michael J Carey
*Assistant Examiner* — Christen A. Sharpless
(74) *Attorney, Agent, or Firm* — Scully, Scott, Murphy & Presser, P.C.

(57) ABSTRACT

An endoscope system includes an illuminator comprising a light source adapted to emit light of a light amount corresponding to a magnitude of supply energy, the illuminator configured to emit the light in a form of illumination light for illuminating a subject; an imager configured to image the subject to acquire an image; a controller configured to control the illuminator by adjusting the magnitude of the supply energy within a range less or equal to a maximum supply value, to bring brightness of the illumination light close to a target value; and a setter configured to set the maximum supply value according to a temperature of the light source.

16 Claims, 11 Drawing Sheets

(52) U.S. Cl.
CPC ................. *A61B 1/05* (2013.01); *A61B 1/06* (2013.01); *A61B 1/0676* (2013.01); *A61B 1/00009* (2013.01)

(56) References Cited

U.S. PATENT DOCUMENTS

| | | | | |
|---|---|---|---|---|
| 2010/0228089 | A1* | 9/2010 | Hoffman | H01S 5/06216 600/182 |
| 2012/0016200 | A1* | 1/2012 | Seto | A61B 1/05 600/180 |
| 2012/0277534 | A1* | 11/2012 | Masaki | A61B 1/00066 600/145 |
| 2014/0276784 | A1* | 9/2014 | Ward | A61L 2/14 606/41 |
| 2016/0218727 | A1* | 7/2016 | Maki | H01S 1/06 |

FOREIGN PATENT DOCUMENTS

| | | | | |
|---|---|---|---|---|
| JP | 2009-189473 A | 8/2009 | | |
| JP | 2012-66015 A | 4/2012 | | |
| JP | 2012120764 A | * | 6/2012 | |
| JP | 2015-170708 A | | 9/2015 | |
| WO | WO-2015005277 A1 | * | 1/2015 | ........... A61B 1/0002 |

OTHER PUBLICATIONS

Japanese Office Action dated Feb. 4, 2020 in Japanese Patent Application No. 2018-523107.

Chinese Office Action dated Oct. 23, 2020 in Chinese Patent Application No. 201680086757.4.

English translation of International Preliminary Report on Patentability dated Dec. 27, 2018 together with the Written Opinion received in related International Application No. PPCT/JP2016/067810.

Japanese Office Action dated Jul. 2, 2019 in Japanese Patent Application No. 2018-523107.

\* cited by examiner

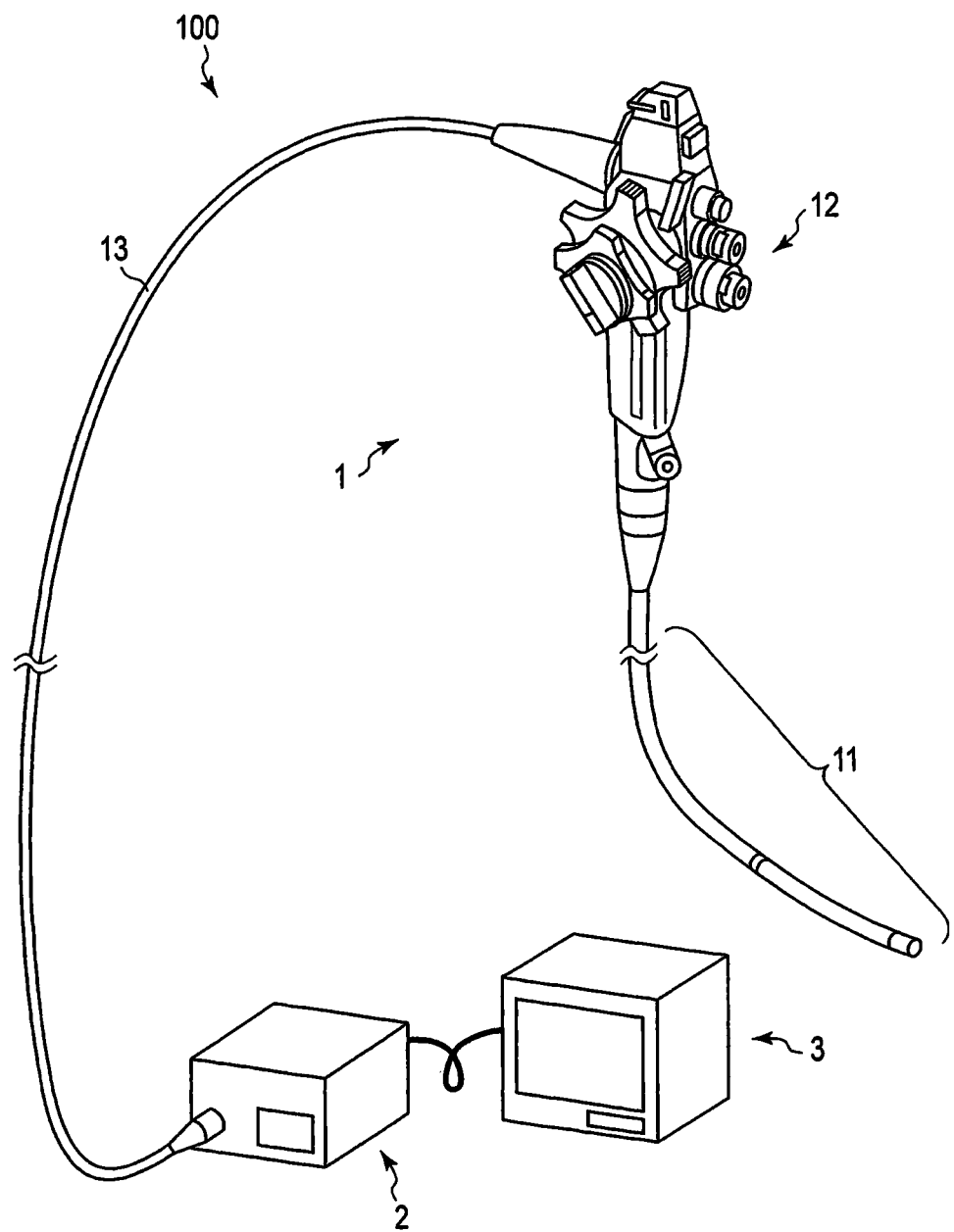
F I G. 1

ENDOSCOPE SYSTEM

CROSS-REFERENCE TO RELATED APPLICATIONS

This application is a Continuation Application of PCT Application No. PCT/JP2016/067810, filed Jun. 15, 2016, the entire contents of all of which are incorporated herein by reference.

BACKGROUND OF THE INVENTION

1. Field of the Invention

The present invention relates to an endoscope system.

2. Description of the Related Art

An endoscope system is adapted to illuminate a subject with light generated by a light source, e.g., a laser light source, and to acquire images of the subject.

For example, Jpn. Pat. Appln. KOKAI Publication No. 2012-66015 discloses a technique for adjusting the temperature of a laser light source using a temperature adjustment device, such as a Peltier device, to reduce variations in temperature of the light source to consequently suppress variations in light emission with high accuracy.

BRIEF SUMMARY OF THE INVENTION

According to an aspect of the invention, an endoscope system includes an illuminator comprising a light source adapted to emit light of a light amount corresponding to a magnitude of supply energy, the illuminator configured to emit the light in a form of illumination light for illuminating a subject; an imager configured to image the subject to acquire an image; a controller configured to control the illuminator by adjusting the magnitude of the supply energy within a range less or equal to a maximum supply value, to bring brightness of the illumination light close to a target value; and a setter configured to set the maximum supply value according to a temperature of the light source.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view showing a general configuration for an endoscope system according to a first embodiment.

DETAILED DESCRIPTION OF THE INVENTION

Figure 2:
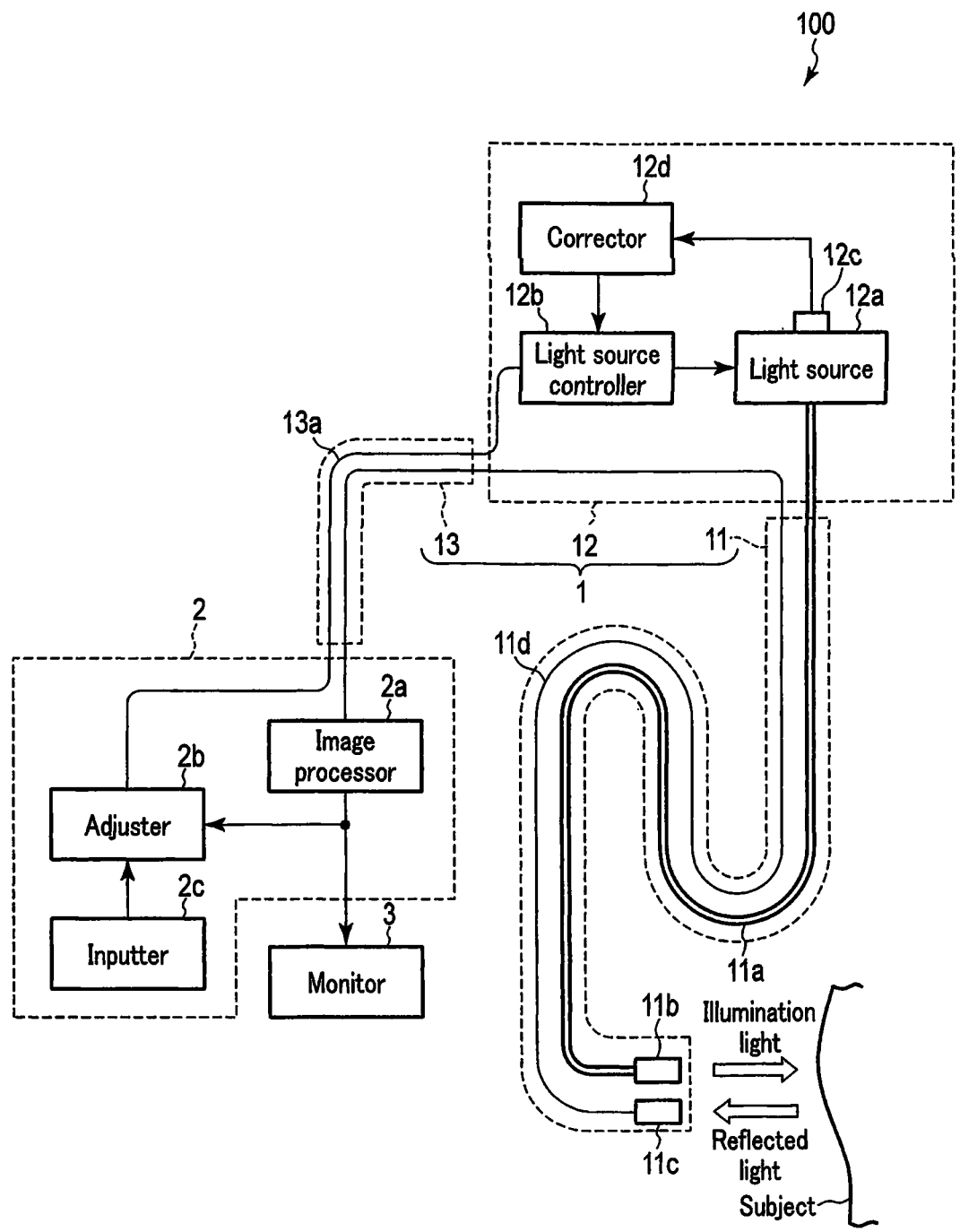
FIG. 2 is a diagram showing an internal configuration for the endoscope system presented in FIG. 1.

Hereinafter, certain embodiments of the invention will be described in detail with reference to the drawings.

First Embodiment

FIG. 1 is a perspective view showing a general configuration for an endoscope system 100 according to the first embodiment.

The endoscope system 100 includes an endoscope apparatus 1, a central part 2, and a monitor 3.

The endoscope apparatus 1 images the inside of canals, such as a lumen of a patient, etc. The endoscope apparatus 1 is typically an endoscope apparatus for medical use, such as an upper gastrointestinal endoscope, a large intestine endoscope, an ultrasonic endoscope, a cystoscope, pyeloscope, or a bronchoscope, or an endoscope apparatus for industrial use. Nevertheless, the endoscope apparatus 1 may be applied to any canals as an imaging subject, and may be used for purposes different from medical or industrial purposes. Also, the endoscope apparatus 1 may be a direct-view type or a side-view type. The following description will assume the endoscope apparatus 1 to be for medical use.

The endoscope apparatus 1 includes an insertion module 11, an operation module 12, and a universal cord 13. The proximal end of the insertion module 11 is coupled with the operation module 12. The distal end of the insertion module 11 is adapted for insertion into a body cavity for imaging operations. The operation module 12 is coupled with the distal end of the universal cord 13. The universal cord 13 is furnished with a connector (not illustrated) at its proximal end, which allows the universal cord 13 to be detachably connected to the central part 2.

The insertion module 11 is sectioned into a rigid front portion, a bending portion, and a flexible tube portion, as viewed from the distal end to the proximal end of the insertion module 11. The rigid front portion does not easily deform. The bending portion is bendable in desired directions in response to an operator operating the operation module 12. With the bending portion bending, the position and the orientation of the rigid front portion are changed. The flexible tube portion has a desired flexibility and bends upon receipt of an external force.

The operation module 12 is adapted to be gripped by an operator. The operation module 12 includes an angle knob and other components in a known arrangement for changing the bending state of the bending portion of the insertion module 11.

The insertion module 11 and the operation module 12 are provided with a gas/fluid flow channel and a treatment instrument channel both extending from the operation module 12 to the distal end of the insertion module 11 in a known manner. The gas/fluid flow channel is used for communicating gas or fluid between the operation module 12 and the distal end of the insertion module 11. The treatment instrument channel opens at each of the operation module 12 and the distal end of the insertion module 11. The treatment instrument channel guides a treatment instrument inserted from the operation module 12 to the distal end of the insertion module 11.

The universal cord 13 conveys various signals (described later) between the operation module 12 and the central part 2.

The central part 2 processes images taken by the endoscope apparatus 1 as described later.

The monitor 3 displays images processed by the central part 2.

FIG. 2 is a diagram showing an internal configuration for the endoscope system 100.

The insertion module 11 includes an optical fiber 11a, an optical converter 11b, an imager 11c, and a signal cable 11d. The operation module 12 includes a light source 12a, a light source controller 12b, a temperature sensor 12c, and a corrector 12d. The universal cord 13 includes the signal cable 11d and a signal cable 13a. The central part 2 includes an image processor 2a, an adjuster 2b, and an inputter 2c.

The optical fiber 11a has one end connected to the light source 12a. The other end of the optical fiber 11a is attached with the optical converter 11b. The light source 12a emits primary light. Typically, a laser diode is employed as the light source 12a. However, the light source 12a may be of any type as long as it is adapted to emit primary light that allows for obtaining light suitable for imaging operations, namely, obtaining illumination light as will be described. The light source 12a may include multiple light-emitting devices. The optical fiber 11a transmits the primary light emitted from the light source 12a to the optical converter 11b. The optical converter 11b converts the primary light having been transmitted by the optical fiber 11a into illumination light for emission toward a subject. The optical converter 11b includes, as one example, a wavelength-converting function. The illumination light is emitted from the distal end of the optical fiber 11a toward the subject. The optical converter 11b may include a fluorescent substance to emit fluorescence using the primary light as excitation light. In the instance where the primary light is laser light, the optical converter 11b may include a light-diffusing function to widen the spreading angle of the primary light in order to obtain illumination light having a low invasiveness to subjects. The optical converter 11b may also include a phase-converting and coherence-reducing function in order to prevent speckles when the primary light is laser light, for example. The optical converter 11b is disposed at the rigid front portion. The light source 12a, the optical fiber 11a, and the optical converter 11b therefore realize a function as an illuminator adapted to emit the illumination light for illuminating a subject.

The imager 11c converts an image formed by the light reflected from the subject, that is, an image of the subject, into an electric signal (hereinafter, "image signal"). The imager 11c sends the image signal to the signal cable 11d. The imager 11c is, for example, a charge-coupled device (CCD) imager or a complementary metal oxide semiconductor (CMOS) imager. The signal cable 11d extends to the image processor 2a in the central part 2, through the insertion module 11, the operation module 12, and the universal cord 13. The image signal is therefore transmitted to the image processor 2a through the signal cable 11d. The imager 11c is an example of an imager adapted to image a subject to acquire images.

The image processor 2a processes the image signal sent from the imager 11c through the signal cable 11d, and generates an image for the monitor 3 to display. For example, when the image signal is of a single-plate color image, the image processor 2a subjects the image signal to demosaic (synchronization) processing to generate a so-called three-plate color image where color signals representing three colors (i.e., R, G, and B) are all available for each pixel. The image processor 2a also performs processing including color balance adjustment, gamma conversion, and color conversion, etc. for the generated color image. Furthermore, the image processor 2a converts the image into a signal format for display on the monitor 3, and outputs the signal to the monitor 3. The monitor 3 displays the image generated by the image processor 2a. As the monitor 3, while any of the various known display devices may be adopted discretionarily, use of a color liquid crystal display device is assumed as an example. Note, however, that the image processor 2a and the monitor 3 may be adapted to process and display monochrome images.

The image generated by the image processor 2a is also input to the adjuster 2b. The adjuster 2b detects brightness of the subject on the color image. Hereinafter, the brightness detected by the adjuster 2b will be referred to as a "detected brightness". The adjuster 2b is connected to the inputter 2c. The inputter 2c inputs information for a target value of the brightness of the subject on the color image, that is, target brightness information, in response to an operation by an operator, or the inputter 2c inputs the target brightness information from another device (not illustrated). By the input of the target brightness information, the inputter 2c gives the target brightness information to the adjuster 2b. The adjuster 2b generates a light-amount control signal for bringing the detected brightness closer to the brightness corresponding to the target brightness information. The adjuster 2b outputs the light-amount control signal to the signal cable 13a. The signal cable 13a extends to the light source controller 12b in the operation module 12 through the universal cord 13. The light-amount control signal is therefore transmitted to the light source controller 12b through the signal cable 13a.

The light source controller 12b controls the light source 12a so that the light amount of the illumination light is controlled based on the light-amount control signal. To control the light source 12a, the light source controller 12b takes into account a correction value generated by the corrector 12d, as will be described.

The temperature sensor 12c detects the temperature of the light source 12a. Therefore, the temperature sensor 12c an example of a first determiner configured to determine the temperature of the light source 12a. The temperature sensor 12c may be discretionarily selected from various devices, such as a thermistor, a thermocouple, and a resistance temperature device (RTD), as long as these devices are adapted to output an electric signal according to a detected value of the temperature. Preferably, the temperature sensor 12c is provided adjacent to the light source 12a via, for example, a metal having a high thermal conductivity, so that the temperature of the light source 12a can be detected with high accuracy. The temperature detected by the temperature sensor 12c is given to the corrector 12d.

The corrector 12d generates the correction value for addressing a change in the relationship between a current applied to the light source 12a and the optical output of the light source 12a, caused due to an ambient temperature. The corrector 12d gives the generated correction value to the light source controller 12b.

Next, operations of the endoscope system 100 configured as above will be described. Note that, by way of example, the description will be given of an instance where a laser diode is employed as the light source 12a.

(Basic Operations)

The light source 12a operates upon application of an activate current and emits laser light as primary light. The primary light is transmitted to the optical converter 1ib by the optical fiber 11a. Subsequently, the primary light is converted into illumination light by the optical converter 11b and the obtained illumination light is emitted from the distal end of the insertion module 11. When, as shown in FIG. 2, a subject faces the distal end of the insertion module 11, the subject is illuminated by the illumination light.

An image of the subject, formed from the light reflected from the subject, is taken by the imager 11c. The imager 11c then outputs an image signal indicative of the image of the subject to the signal cable 11d. This image signal is sent to the image processor 2a through the signal cable 11d. The image processor 2a generates a color image based on this image signal. The monitor 3 displays the color image.

(Activate and Light Control for the Light Source 12a)

The optical output of the light source 12a is approximately zero when the activate current is below a threshold. When the activate current is equal to or greater than the threshold, the optical output of the light source 12a has a magnitude that is substantially proportional to the magnitude of the activate current. In other words, light source 12a adapted to emit the light of a light amount corresponding to a magnitude of supply energy. In this regard, the light source 12a has a temperature characteristic, and the threshold varies depending on the temperature. As such, even with the activate current of a given magnitude applied, a different optical output could be produced depending on the temperature of the light source 12a.

Accordingly, the adjuster 2b and the light source controller 12b acquire the detected brightness as a brightness of the subject on the color image generated by the image processor 2a, and control the light source 12a so that the detected brightness will approach a target value.

More specifically, the adjuster 2b generates the light-amount control signal as a signal indicative of a difference value of the detected brightness with respect to the target value. That is, for example, the adjuster 2b generates the light-amount control signal as a signal indicating a value obtained by subtracting the target value from the detected brightness. However, the light-amount control signal may be any signal so long as it can indicate the degree to which the optical output of the light source 12a should be changed. Therefore, the adjuster 2b may also generate the light-amount control signal as a signal indicative of a ratio of the detected brightness to the target value. In this case, for example, the adjuster 2b generates the light-amount control signal as a signal indicating a value obtained by dividing the detected brightness by the target value.

The light source controller 12b applies the activate current, which is pulsed, to the light source 12a. For the application of this activate current, known current-outputting type activate circuitry may be employed. The light source controller 12b controls the optical output of the light source 12a by increasing or decreasing a time width (pulse width) of the pulse-ON period based on the light-amount control signal from the adjuster 2b. The light source controller 12b determines this time width as a value within a range from a predetermined minimum value to a predetermined maximum value of the ON period. In relation to this, it is assumed that the light source controller 12b adopts a constant cycle for turning on the pulses, regardless of the light-amount control signal. The light source controller 12b also sets the pulse-ON period within one cycle to be a value from 0% to 100%. Note that the minimum value of the ON period is not limited to 0%, but may be set to any value between 0% and 100%. For example, a designer, etc. of the endoscope system 100 may preset the minimum value. Furthermore, the maximum value of the ON period is not limited to 100%, but may be set to any value greater than the minimum value and between 0% and 100%. For example, the designer, etc. of the endoscope system 100 may preset the maximum value. Note that the light source controller 12b may control the optical output of the light source 12a by changing one or more conditions including a pulse width of the current, a pulse number of the current per unit time, a pulse density of the current per unit time, and a pulse amplitude of the current.

Additionally, as the imager 11c, use of a device adapted for exposure control with a rolling shutter can be assumed. In this case, the light source controller 12b may perform the pulse activating so that the light is on for a period during which none of the reading lines in the imager 11c are subject to a reading operation, that is, for the period of exposure for all the lines. As a supplementary note, the rolling shutter refers to a technique that sequentially starts, line by line, one-frame period or one-field period exposure of imaging elements associated with multiple lines in the imager 11c, and reads the lines one after another upon each of the lines having undergone a predetermined exposure period since the start of the exposure.

The light source controller 12b sets an amplitude of the pulse to be within a range that will render the optical output equal to, or lower than, a predetermined maximum output value Plim. The amplitude of the pulse corresponds to a current value of the activate current when the pulse is on. The maximum output value Plim is pre-set by a setting entity, which may be a designer, etc. of the endoscope system 100, for example. The setting entity sets the maximum output value Plim in consideration of, for example, the durability, etc. of the optical converter 1ib so that the maximum output value Plim represents a value that permits the optical converter 11b to continue its normal operation with the optical output of the corresponding magnitude. In another option, the setting entity sets the maximum output value Plim based on the emission characteristics of the illumination light emitted from the optical converter 1ib. That is, the setting entity makes this setting so that the illumination light for emission will fall within a range that incurs a small degree of influence on subjects. For example, the setting entity estimates the largest light intensity of illumination light having the degree of influence on a subject within a tolerable range, and adopts, as the maximum output value Plim, an amount of the primary light that produces the illumination light of the determined largest light intensity. In yet another option, the setting entity sets the maximum output value Plim so as to operate with a light amount that does not cause solidification of a foreign substance attached to an illumination-light emission port at the distal end of the insertion module 11, or so as to keep the temperature rise due to an attached foreign substance absorbing the illumination light within a negligible range. It is not a requisite to set the maximum output value Plim to be an ultimate value determined based on various conditions as described above, but the maximum output value Plim may be moderately set with a margin for the ultimate value. The light source controller 12b adapted to operate as above functions as a controller for controlling the illuminator.

In this manner, the magnitude of the optical output of the light source 12a is feedback-controlled so that the brightness of the subject on the color image approaches the target brightness. Note that the brightness of the subject on the color image involves a variation in magnitude of the optical output which is due to the temperature characteristic of the light source 12a. Therefore, for the adjustment of the optical output of the light source 12a, the feedback control as discussed above compensates for the temperature characteristic of the light source 12a.

Meanwhile, the pulse amplitude for yielding the optical output of the maximum output value Plim varies depending on the temperature of the light source 12a. As such, if the maximum value of the activate current (hereinafter, "maximum current value") is a fixed value, the optical output could exceed the maximum output value Plim and deteriorate the optical converter. One preventive measure against this is to set the maximum current value to be sufficiently small so that the optical output will not exceed the maximum output value Plim at any temperature within the assumed temperature range. However, this measure would lower the optical output more than necessary, and could hamper the brightness of the subject reaching the target value.

(Setting the Maximum Current Value)

Therefore, the light source controller 12b adopts, as the maximum current value, a value obtained by adding a correction value to a predetermined reference maximum value, and sets the pulse amplitude to be equal to or lower than this maximum current value. More specifically, the light source controller 12b sets a value of a predetermined ratio to the maximum current value, for example, a value of 80%, to be the pulse amplitude. The light source controller 12b may also set a value equal to the maximum current value, to be the pulse amplitude. The light source controller 12b therefore functions as a second determiner adapted to determine the maximum current value as an upper limit of supply.

The corrector 12d generates the correction value based on the detected temperature at the temperature sensor 12c in the following manner.

The corrector 12d includes a memory. The corrector 12d stores table data in the memory. The table data describes correction values in association with multiple temperatures, respectively. The correction values are each pre-settable by, for example, a designer, etc. of the endoscope system 100 as a difference between the maximum current value to be set in the case of the associated temperature being the temperature of the light source 12a, and the predetermined reference maximum value.

Figure 3:
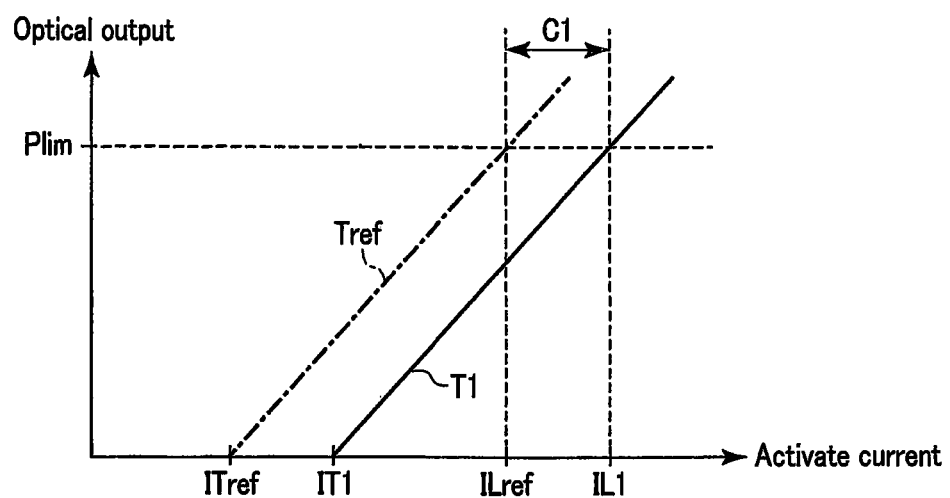
FIG. 3 is a diagram showing an example of how a correction value is set.

FIG. 3 is a diagram showing an example of how the correction value is set.

In FIG. 3, the dashed-dotted line shows the relationship between the activate current and the optical output when the light source 12a is at a predetermined reference temperature Tref. The reference maximum value, which is the maximum current value for the reference temperature Tref, is given as ILref according to the characteristic indicated by this dashed-dotted line. On the other hand, the solid line shows the relationship between the activate current and the optical output when the light source 12a is at a temperature T1. The maximum current value to be set for the temperature T1 is given as IL1 according to the characteristic indicated by the solid line. The correction value for the temperature T1 is then set to be a value C1 obtained by [IL1−ILref].

Therefore, the light source controller 12b functioning as the above-described second determiner, the temperature sensor 12c as first determiner adapted to determine the temperature of the light source 12a, and the corrector 12d together realize a function as a setter adapted to set the maximum current value according to the temperature of the light source 12a.

The maximum current values at the respective temperatures are measured values. The maximum current values may also be obtained through simulation, or may be determined based on the specs published by the manufacturer of the device used as the light source 12a.

The corrector 12d selects the temperature closest to the temperature detected by the temperature sensor 12c from among the temperatures described in the table data, and reads the correction value associated with the selected temperature from the table data. The corrector 12d then outputs the read correction value to the light source controller 12b.

Note that the light source controller 12b may set the pulse amplitude to be equal to or greater than the minimum current value. The minimum current value (minimum supply value) in this case would be the lowest value of the activate current for the light source 12a to emit laser light, namely, the threshold current value, or a current value obtained by adding a margin to the threshold current value. Since the threshold current value for the light source 12a also varies with temperature, the minimum current value should preferably be changed as well, according to the temperature of the light source 12a. For example, the light source controller 12b sets the minimum current value based on the maximum current value having been set as described above. One exemplary setting in this case would be that the light source controller 12b sets the minimum current value to have a predetermined difference from, or a predetermined ratio to, the maximum current value. The light source controller 12b may also add a correction value generated by the corrector 12d to a reference value of the minimum current value, obtained in a similar manner as described above by taking into account the optical output characteristic of the light source 12a at the reference temperature Tref, and set the resultant value as the minimum current value.

(Effects)

According to the endoscope system 100, the detected brightness as a brightness of the subject on the color image is acquired, and the light source 12a is controlled to bring the detected brightness closer to the target value. Therefore, the optical output at the present temperature is adjusted to have a magnitude for making brightness of the subject on the color image the target value, and the brightness of the subject on the color image can be kept at the target value.

Also, in the endoscope system 100, the maximum current value is corrected according to the temperature of the light source 12a, and this prevents the occurrence of a problem of excessive optical output increase. The endoscope system 100 therefore requires no temperature adjustment device such as a Peltier device for adjusting the temperature of the light source 12a, and is free from power consumption due to temperature adjustment device.

Second Embodiment

Figure 4:
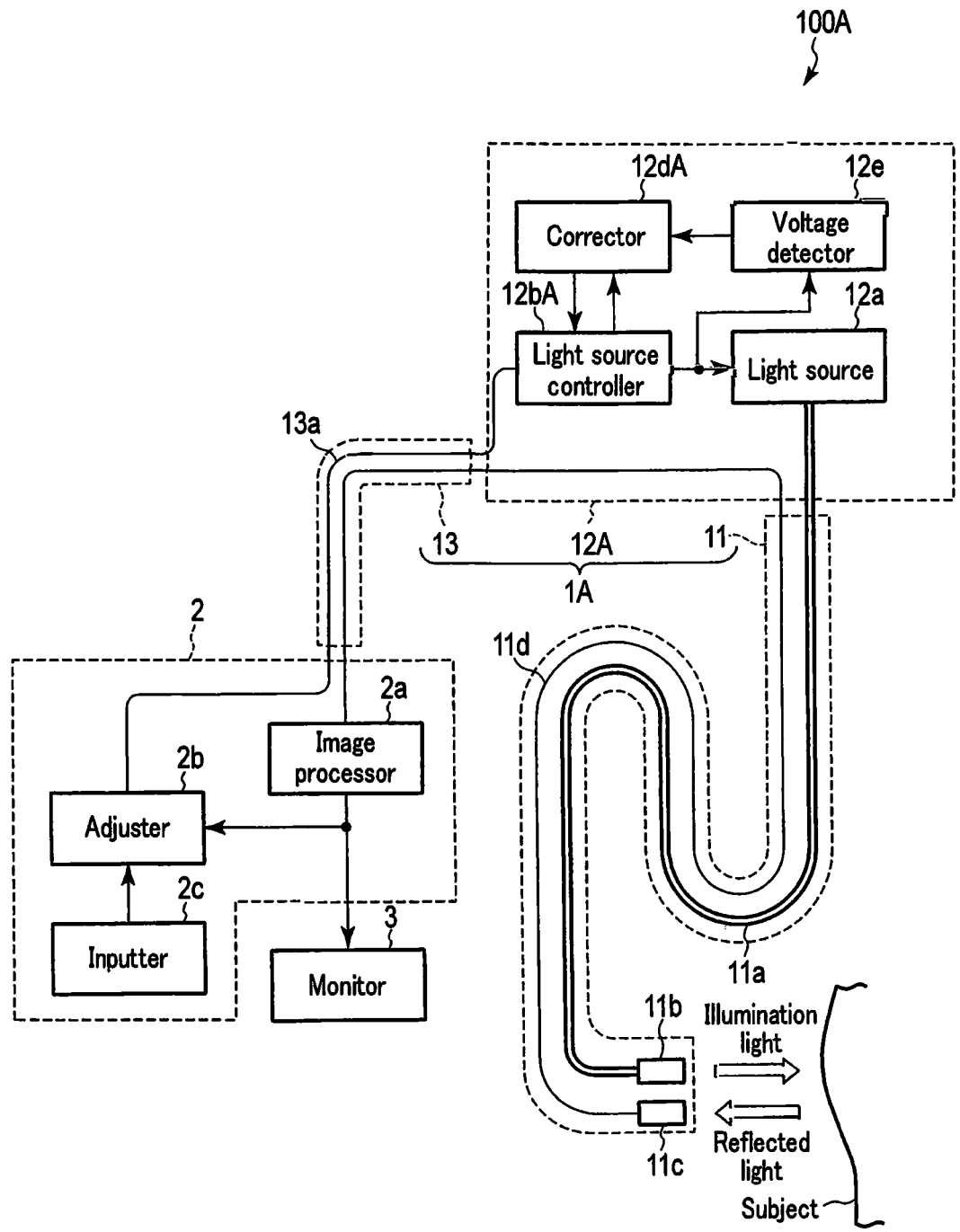
FIG. 4 is a block diagram showing an internal configuration for an endoscope system according to a second embodiment.

FIG. 4 is a block diagram showing an internal configuration for an endoscope system 100A according to the second embodiment. The elements shown in FIG. 4, which are equivalent to the corresponding elements shown in FIG. 2, are denoted by the same reference symbols, and their detailed descriptions will be omitted.

The endoscope system 100A includes an endoscope apparatus 1A, the central part 2, and the monitor 3. That is, the endoscope system 100A includes the endoscope apparatus 1A in place of the endoscope apparatus 1 in the endoscope system 100.

The endoscope apparatus LA includes the insertion module 11, an operation module 12A, and the universal cord 13. That is, the endoscope apparatus 1A includes the operation module 12A in place of the operation module 12 in the endoscope apparatus 1.

The operation module 12A includes the light source 12a, a light source controller 12bA, a corrector 12dA, and a voltage detector 12e. That is, the operation module 12A includes the light source controller 12bA and the corrector 12dA in place of the light source controller 12b and the corrector 12d in the operation module 12, does not include the temperature sensor 12c, and additionally includes the voltage detector 12e.

The light source controller 12bA includes the same function as the light source controller 12b according to the first embodiment. In addition, the light source controller 12bA has a function of notifying the corrector 12dA of the magnitude of the activate current being applied to the light source 12a. The voltage detector 12e detects an activate voltage that is attribute to application of the activate current from the light source controller 12b to the light source 12a. The corrector 12dA determines the temperature of the light source 12a based on the activate current notified from the light source controller 12bA and the activate voltage detected by the voltage detector 12e. Therefore, the corrector 12dA and the voltage detector 12e together realize a function as a first determiner. The corrector 12dA outputs a correction value according to the determined temperature.

Next, operations of the endoscope system 100A configured as above will be described. In the operations of the endoscope system 100A, what is different from the operations of the endoscope system 100 is an operation for determining the correction value. Accordingly, the description will focus on the operation for determining the correction value.

(Determining the Correction Value)

The corrector 12dA includes a memory. The corrector 12dA stores first and second table data in the memory. The first table data describes correction values in association with multiple temperatures, respectively. In other words, the first table data is the table data stored by the corrector 12d in the first embodiment. The second table data describes many combinations of the activate current and the activate voltage, in association with multiple temperatures. The second table data is pre-settable by, for example, a designer, etc. of the endoscope system 100A.

Figure 5:
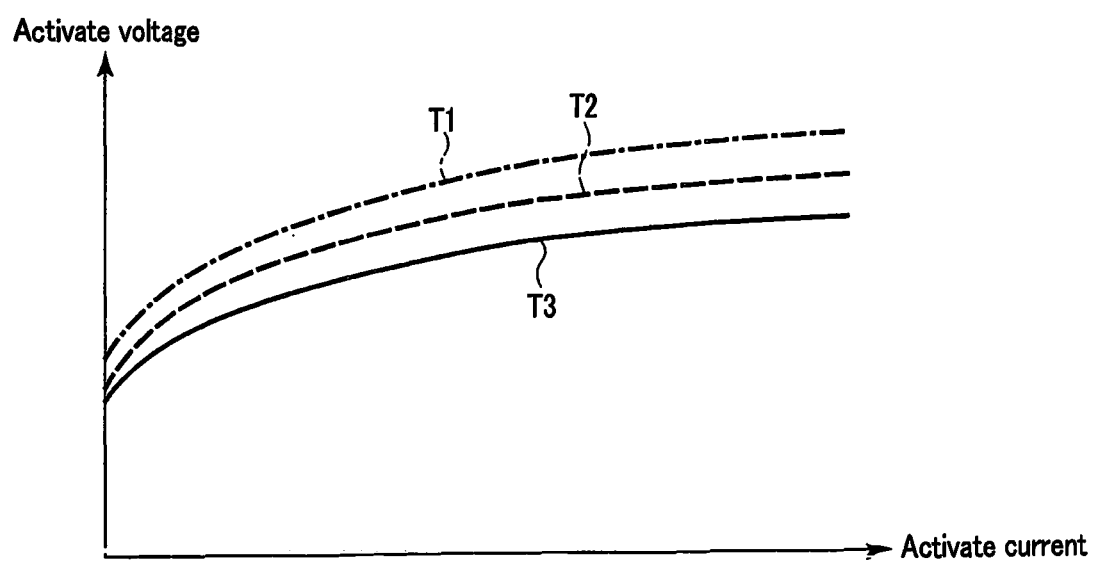
FIG. 5 is a diagram showing a relationship between an activate current and an activate voltage for the light source presented in FIG. 4.

FIG. 5 is a diagram showing a relationship between the activate current and the activate voltage for the light source 12a.

FIG. 5 depicts a change in the activate voltage when the activate current applied to the light source 12a is changed.

As shown in this figure, when a laser diode is employed as the light source 12a, an increase or decrease of the activate voltage accompanies the increase or decrease of the activate current applied to the light source 12a, and the degree of change varies depending on the temperature of the light source 12a. One example is, as shown in FIG. 5, that the lower the temperature of the light source 12a, the greater the degree. In the case shown in FIG. 5, the temperatures T1, T2, and T3 of the light source 12a are in the relationship T1<T2<T3.

The designer, etc. writes the association between the temperature and the combination of the activate current and the activate voltage, revealed from such a characteristic of the light source 12a, into the second table data.

The corrector 12dA selects the combination that is the most similar to the combination of the activate current notified from the light source controller 12bA and the activate voltage detected by the voltage detector 12e, from among the combinations described in the second table data. The corrector 12dA then determines the temperature of the light source 12a to be the temperature associated with the selected combination. The corrector 12dA handles the thus-determined temperature in the same manner as the temperature detected by the temperature sensor 12c, and subsequently outputs the correction value to the light source controller 12bA through the same processing as performed by the corrector 12d in the first embodiment.

(Effects)

With the endoscope system 100A, the effects as achieved by the endoscope system 100 in the first embodiment can be achieved likewise. Furthermore, according to the endoscope system 100A, the temperature sensor 12c as provided in the endoscope system 100 is not required.

Third Embodiment

Figure 6:
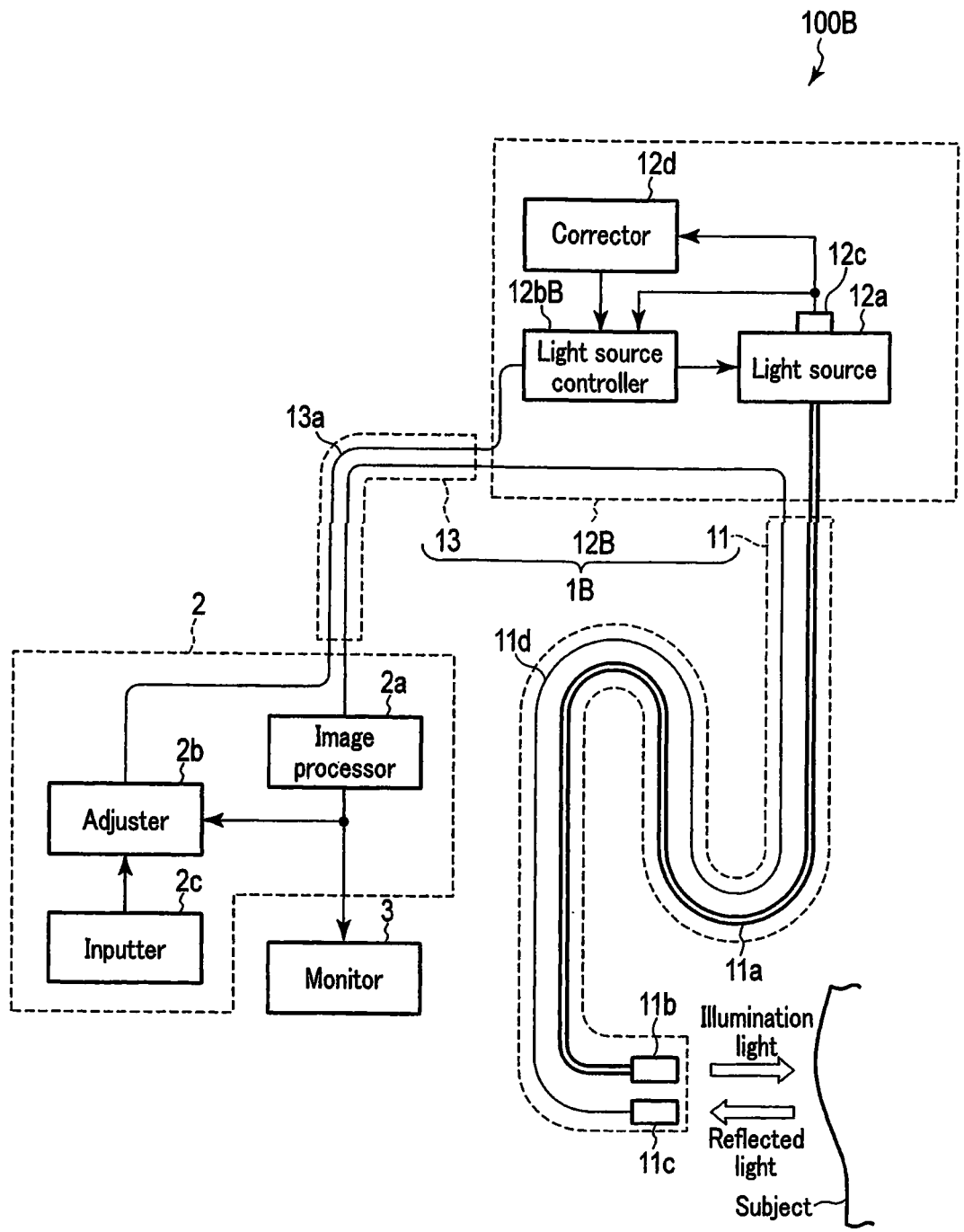
FIG. 6 is a block diagram showing an internal configuration for an endoscope system according to a third embodiment.

FIG. 6 is a block diagram showing an internal configuration for an endoscope system 100B according to the third embodiment. The elements shown in FIG. 6, which are equivalent to the corresponding elements shown in FIG. 2, are denoted by the same reference symbols, and their detailed description will be omitted.

The endoscope system 100B includes an endoscope apparatus 1B, the central part 2, and the monitor 3. That is, the endoscope system 100B includes the endoscope apparatus 1B in place of the endoscope apparatus 1 in the endoscope system 100.

The endoscope apparatus 1B includes the insertion module 11, an operation module 12B, and the universal cord 13. That is, the endoscope apparatus 1B includes the operation module 12B in place of the operation module 12 in the endoscope apparatus 1.

The operation module 12B includes the light source 12a, a light source controller 12bB, the temperature sensor 12c, and the corrector 12d. That is, the operation module 12B includes the light source controller 12bB in place of the light source controller 12b in the operation module 12.

The light source controller 12bB includes the same function as the light source controller 12b according to the first embodiment. However, the light source controller 12bB has a function of setting the maximum current value with consideration of the efficiency of the light source 12a. The light source controller 12bB includes a memory. The light source controller 12bB stores later-described third table data in the memory.

Next, operations of the endoscope system 100B configured as above will be described. In the operations of the endoscope system 100B, what is different from the operations of the endoscope system 100 is an operation for determining the maximum current value. Accordingly, the description will focus on the operation for determining the maximum current value.

(Determining the Maximum Current Value)

Figure 7:
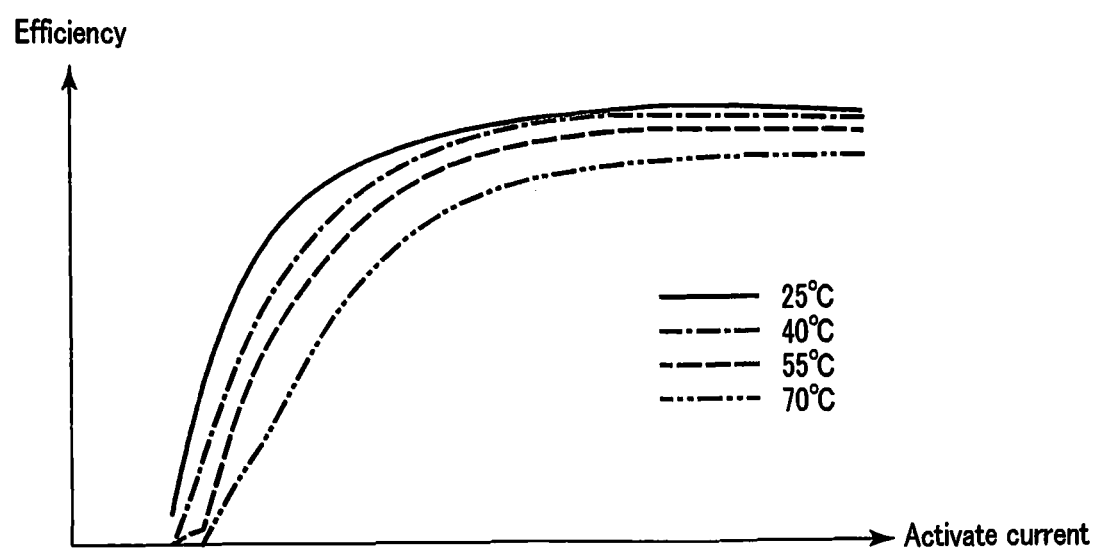
FIG. 7 is a diagram showing a relationship between an activate current and efficiency.

FIG. 7 is a diagram showing a relationship between the activate current and the efficiency.

As shown in FIG. 7, when a laser diode is employed as the light source 12$a$, the efficiency indicating how much optical output can be obtained with respect to a power given by application of a current to the light source 12$a$ varies according to the magnitude of the activate current and the temperature of the light source 12$a$.

Now, the light source controller 12$b$B sets the maximum current value in the same manner as the light source controller 12$b$ in the first embodiment, and adopts it as a first candidate value. Separately from this, the light source controller 12$b$B selects a current value described in the third table data in association with the detected temperature at the temperature sensor 12$c$, as a second candidate value.

The third table data here describes current values of the activate current in association with multiple temperatures, and these current values give the highest efficiency of the light source 12$a$ at the respective associated temperatures. The third table data is pre-settable by, for example, a designer, etc. of the endoscope system 100B with consideration given to the characteristic of the light source 12$a$ as shown in FIG. 7.

The light source controller 12$b$B then sets the first candidate value or the second candidate value, whichever is lower, to be the maximum current value.

(Effects)

With the endoscope system 100B, the effects as achieved by the endoscope system 100 in the first embodiment can be achieved likewise. Furthermore, according to the endoscope system 100B, if it is expected that the light source 12$a$ can efficiently emit light with application of an activate current having a current value lower than the maximum current value as in the first embodiment, the activate current is suppressed to said lower current value. This consequently permits the endoscope system 100B to prevent degradation of efficiency due to an excessive increase of the activate current.

Fourth Embodiment

Figure 8:
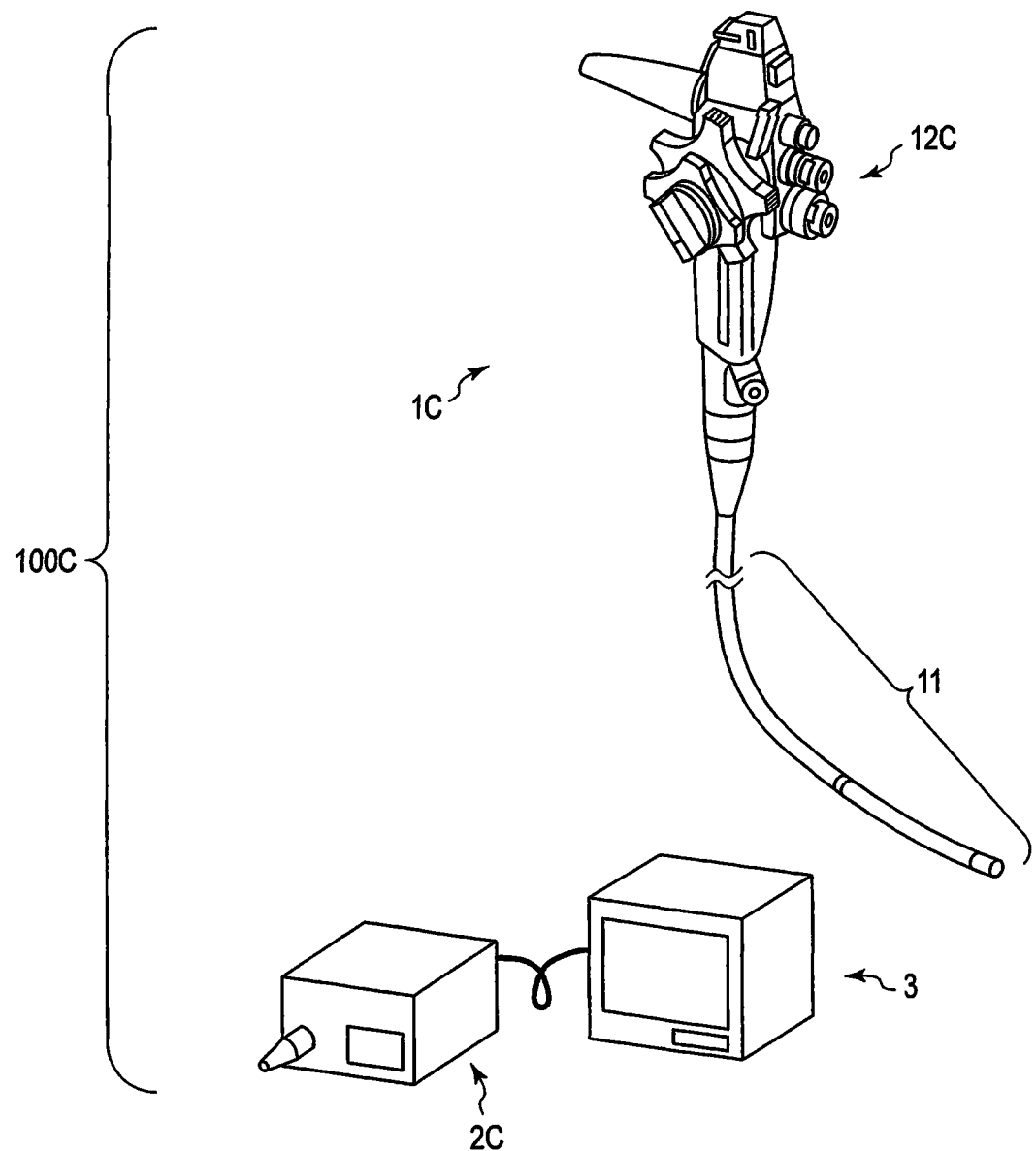
FIG. 8 is a perspective view showing a general configuration for an endoscope system according to a fourth embodiment.
Figure 9:
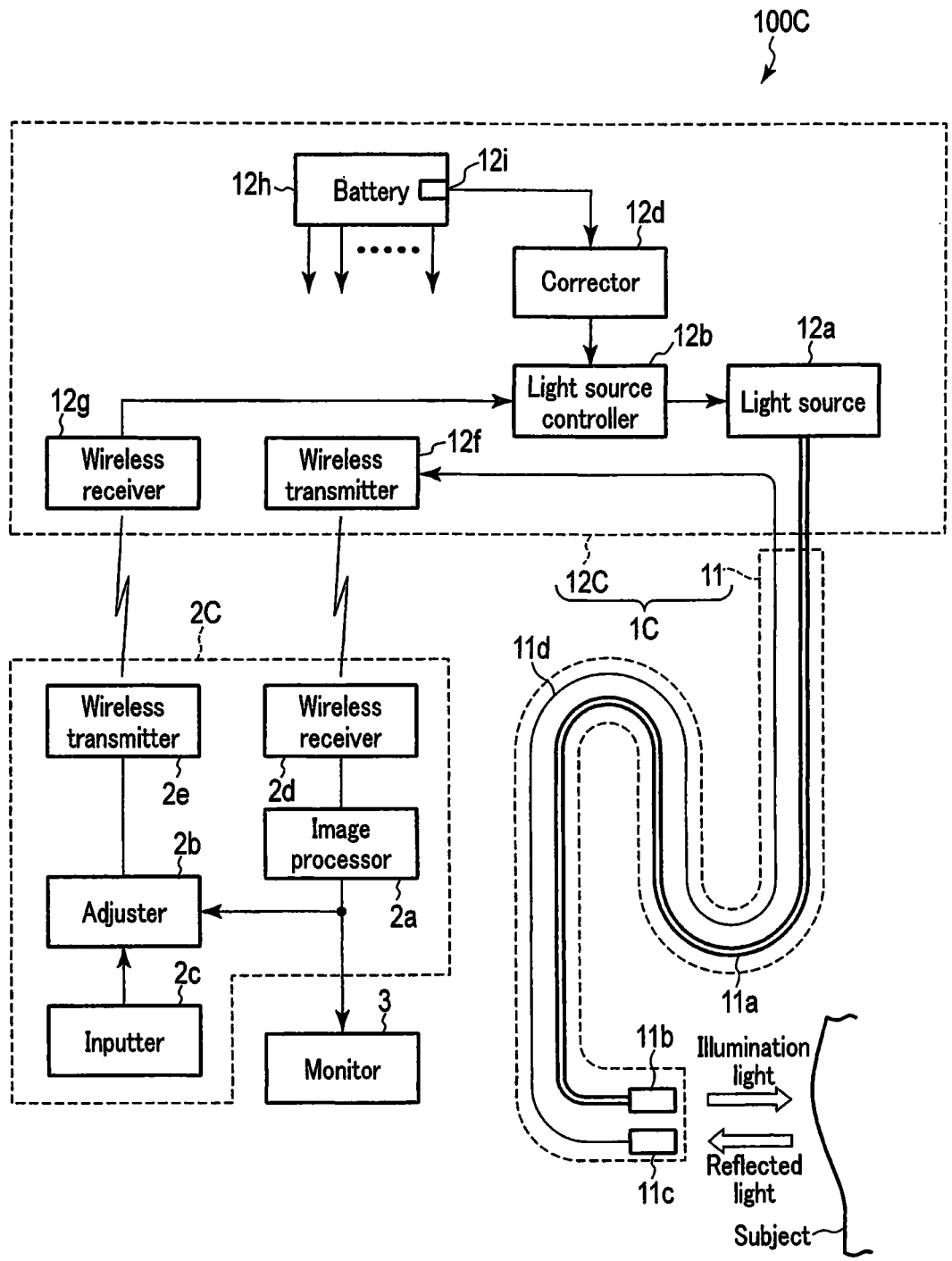
FIG. 9 is a diagram showing an internal configuration for the endoscope system presented in FIG. 8.

FIG. 8 is a perspective view showing a general configuration for an endoscope system 100C according to the fourth embodiment. FIG. 9 is a diagram showing an internal configuration for the endoscope system 100C. The elements shown in FIGS. 8 and 9, which are equivalent to the corresponding elements shown in FIGS. 1 and 2, are denoted by the same reference symbols, and their detailed description will be omitted.

The endoscope system 100C includes an endoscope apparatus 1C, a central part 2C, and the monitor 3. That is, the endoscope system 100C includes the endoscope apparatus 1C and the central part 2C in place of the endoscope apparatus 1 and the central part 2 in the endoscope system 100.

The endoscope apparatus 1C includes the insertion module 11 and an operation module 12C. The endoscope apparatus 1C includes the operation module 12C in place of the operation module 12 in the endoscope apparatus 1, while not including the universal cord 13 in the endoscope apparatus 1.

The operation module 12C includes the light source 12$a$, the light source controller 12$b$, the corrector 12$d$, wireless transmitter 12$f$, a wireless receiver 12$g$, and a battery 12$h$. That is, the operation module 12C does not include the temperature sensor 12$c$ in the operation module 12, but additionally includes the wireless transmitter 12$f$, the wireless receiver 12$g$, and the battery 12$h$. Note, however, that the battery 12$h$ may be replaced by a power source of any type.

The central part 2C includes the image processor 2$a$, the adjuster 2$b$, the inputter 2$c$, a wireless receiver 2$d$, and a wireless transmitter 2$e$. That is, the central part 2C additionally includes the wireless receiver 2$d$ and the wireless transmitter 2$e$, as compared to the central part 2. The wireless receiver 2$d$ and the wireless transmitter 2$e$ may take the form of an external component detachably mounted on the central part 2C.

The end portion of the signal cable 11$d$, opposite to the side connected to the imager 11$c$, does not extend to the central part 2C but is connected to the wireless transmitter 12$f$ in the operation module 12C. Accordingly, the image signal transmitted from the imager 11$c$ is input to the wireless transmitter 12$f$ via the signal cable 11$d$. The wireless transmitter 12$f$ wirelessly transmits the image signal. The wireless receiver 2$d$ receives the image signal wirelessly transmitted from the wireless transmitter 12$f$, and supplies it to the image processor 2$a$. The wireless transmitter 2$e$ wirelessly transmits the light-amount control signal output from the adjuster 2$b$. The wireless receiver 12$g$ receives the light-amount control signal wirelessly transmitted from the wireless transmitter 2$e$, and supplies it to the light source controller 12$b$. In this manner, the endoscope system 100C transmits various signals between the endoscope apparatus 1C and the central part 2C through wireless communications without the universal cord 13. In other words, the endoscope system 100C is configured as a so-called wireless endoscope, in which the endoscope apparatus 1C and the central part 2 wirelessly cooperate with each other. For wireless communications, various modes with various media, such as radio waves, infrared rays, or optical means, can be suitably adopted. Also, the wireless transmitter 12$f$ and the wireless receiver 12$g$, or the wireless receiver 2$d$ and the wireless transmitter 2$e$, may be replaced by a single transmitter/receiver integrating part of the components for shared use, e.g., an antenna.

In the configuration as in the first embodiment, where the endoscope apparatus 1 and the central part 2 are connected to each other using the universal cord 13, power is typically supplied from the central part 2 to the endoscope apparatus 1 via the universal cord 13. In contrast, in the wireless-type configuration as in the present embodiment, power is supplied from the battery 12$h$ to each electric component in the endoscope apparatus 1C. Applicable examples of the battery 12$h$ include a secondary battery such as a lithium ion battery. The battery 12$h$, used particularly for this embodiment, includes a temperature sensor 12$i$ for the temperature management of the battery 12$h$ itself. The temperature sensor 12$i$ is adapted to notify the corrector 12$d$ of the detected temperature.

Next, operations of the endoscope system 100C configured as above will be described. In the operations of the endoscope system 100C, what is different from the operations of the endoscope system 100 is an operation for determining the correction value. Accordingly, the description will focus on the operation for determining the correction value.

(Determining the Correction Value)

The corrector 12d uses the temperature detected at the temperature sensor 12i so that the maximum current value is set in a manner similar to the first embodiment.

That is, the corrector 12d deems the temperature of the battery 12h to be the temperature of the light source 12a for the maximum current value to be set. Therefore, the temperature sensor 12i an example of a first determiner configured to determine the temperature of the light source 12a. To this end, the light source 12a and the battery 12h should preferably have the smallest possible temperature difference therebetween. Thus, it is preferable to arrange the light source 12a and the battery 12h as close to each other as possible. It is further preferable to thermally connect the light source 12a and the battery 12h via a member having a high thermal conductivity.

In consideration of the degree of thermal influence between the light source 12a and the battery 12h, the corrector 12d may correct the temperature detected at the temperature sensor 12i for obtaining the temperature of the light source 12a. More specifically, in consideration of the variation in detected temperature due to heat generated by the battery 12h, processing to offset the influence of the heat generated by the battery 12h may be adopted. That is, the amount of heat generated by the battery 12h itself is estimated based on the magnitude of power or a current output from the battery 12h, and the temperature detected by the temperature sensor 12i is adjusted using the estimated value.

(Effects)

With the endoscope system 100C, the effects as achieved by the endoscope system 100 in the first embodiment can be achieved likewise. Furthermore, according to the endoscope system 100C, the temperature sensor 12c as provided in the endoscope system 100 is not required.

Fifth Embodiment

Figure 10:
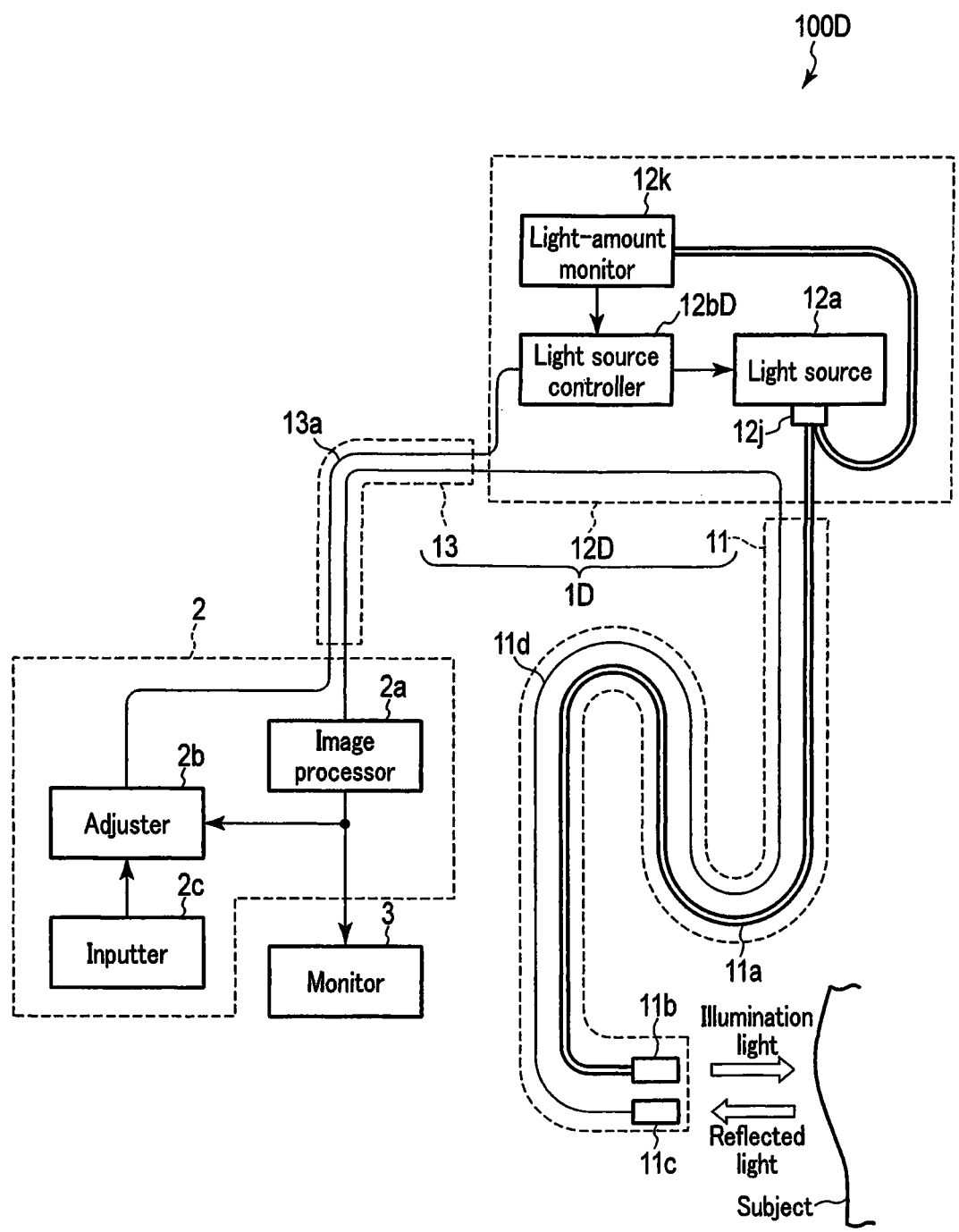
FIG. 10 is a block diagram showing an internal configuration for an endoscope system according to a fifth embodiment.

FIG. 10 is a block diagram showing the internal configuration for an endoscope system 100D according to the fifth embodiment. The elements shown in FIG. 10, which are equivalent to the corresponding elements shown in FIG. 2, are denoted by the same reference symbols, and their detailed descriptions will be omitted.

The endoscope system 100D includes an endoscope apparatus 1D, the central part 2, and the monitor 3. That is, the endoscope system 100D includes the endoscope apparatus 1D in place of the endoscope apparatus 1 in the endoscope system 100.

The endoscope apparatus 1D includes the insertion module 11, an operation module 12D, and the universal cord 13. That is, the endoscope apparatus 1D includes the operation module 12D in place of the operation module 12 in the endoscope apparatus 1.

The operation module 12D includes the light source 12a, a light source controller 12bD, an optical splitter 12j, and a light-amount monitor 12k. That is, the operation module 12D includes the light source controller 12bD in place of the light source controller 12b in the operation module 12, does not include the temperature sensor 12c and the corrector 12d, and additionally includes the optical splitter 12j and the light-amount monitor 12k.

The optical splitter 12j splits the primary light emitted from the light source 12a into two, and causes one light to enter the optical fiber 11a and the other to enter the light-amount monitor 12k. As the optical splitter 12j, an optical coupler, a half mirror, or the like may be employed. The light-amount monitor 12k detects the amount of the incident primary light. As the light-amount monitor 12k, a photodiode may be employed, for example. It is preferable to arrange the light-amount monitor 12k to be thermally separated from heat sources such as the light source, circuitry, etc. It is further preferable to dispose a heat insulating material between the light-amount monitor 12k and heat sources so that the light-amount monitor 12k is thermally isolated. The light source controller 12bD includes the same function as the light source controller 12b according to the first embodiment. However, the light source controller 12bD sets the maximum current value based on the light amount detected by the light-amount monitor 12k.

Next, operations of the endoscope system 100D configured as above will be described. In the operations of the endoscope system 100D, what is different from the operations of the endoscope system 100 is an operation for setting the maximum current value. Accordingly, the description will focus on the operation for setting the maximum current value.

(Setting the Maximum Current Value)

The endoscope apparatus 1D adopts, as a set period, a predetermined period that starts at every predetermined timing. In this set period, the light source controller 12bD sets the maximum current value in a manner as will be described. The set period should preferably avoid periods for imaging a subject. However, the set period may fall within the period for imaging a subject. The timing to start the set period may be discretionarily determined by, for example, a designer of the endoscope system 100D, but the set period should preferably be frequent to the extent that it allows the maximum current value to be appropriately set according to the changes in the temperature of the light source 12a.

In the set period, the light source controller 12bD applies an activate current of a predetermined current value Idrv to the light source 12a. The light source controller 12bD then adopts the value detected at the light-amount monitor 12k for this state as a light-amount detection value Pdet, and sets a maximum current value Ilim using the following expression.

$$Ilim = (Plim - Pdet)/\eta + Idrv$$

In this expression, Plim is an upper limit of the optical output, and $\eta$ is a differential efficiency (increase in optical output per unit current) as the characteristic of the light source 12a.

Figure 11:
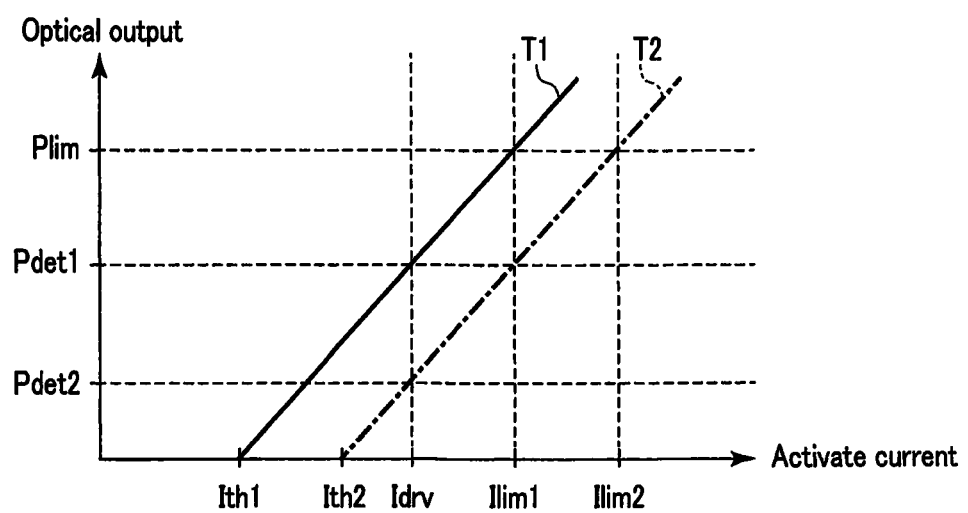
FIG. 11 is a diagram showing a relationship between an activate current and optical output.

FIG. 11 is a diagram showing a relationship between the activate current and the optical output.

As shown in FIG. 11, the light-amount detection value Pdet is Pdet1 at a temperature T1, and it is Pdet2 at a temperature T2. In accordance with such a change in the light-amount detection value Pdet, the maximum current value is set to Ilim1 for the temperature T1 and Ilim2 for the temperature T2.

In other words, the light source controller 12bD functions as a setter adapted to set the maximum current value according to the change in the output light amount, detected by the light-amount monitor 12k according to the temperature of the light source 12a supplied with a current of a predetermined magnitude.

(Effects)

With the endoscope system 100D, the effects as achieved by the endoscope system 100 in the first embodiment can be achieved likewise. Furthermore, according to the endoscope system 100D, the table data as required by the endoscope system 100 is not required.

The embodiments may involve various modifications as will be described.

(1) In each of the embodiments, the following modifications are possible.

(1-1) To provide the light-amount monitor 12k as shown in FIG. 10, or to provide the light-amount monitor 12k in such a manner as to detect the amount of the illumination light emitted from the optical converter 11b, so that the amount of the optical output can be detected. The light source controllers 12b, 12bA, 12bB, and 12bD each control the light source 12a so that the amount detected by the light-amount monitor 12k approaches the target value.

(1-2) To provide, instead of the monitor 3, an image recorder for recording the image generated by the image processor 2a. However, both the monitor 3 and the image recorder may be provided.

(1-3) To transmit the image signal output by the imager 11c in a wireless manner, instead of transmitting the image signal through the signal cable 11d. In this case, the image signal may be transmitted from the imager 11c wirelessly and directly to the central part 2 or 2C. The image signal may also be wirelessly transmitted from the imager 11c to the operation module 12, 12A, 12B, 12C, or 12D, and then transferred to the central part 2 or 2C through the signal cable.

(1-4) To configure the light source controllers 12b, 12bA, 12bB, and 12bD to each adjust the pulse-ON period with the current value of the activate current fixed, so that the optical output will be controlled. In this case, the light source controllers 12b, 12bA, and 12bB each correct the reference value of the maximum ON period using the correction value given from the corrector 12d or 12dA, to set the maximum value of the ON period.

(1-5) To adopt the maximum current values set by the respective techniques in one of the embodiments, and at least one other embodiment, as candidate values, and set the minimum value among these candidate values to be the maximum current value.

(2) In the first to fourth embodiments, the following modifications are possible.

(2-1) In the instance where the light source 12a includes multiple light-emitting devices, to configure the light source controller 12b to individually set the maximum current value for each of the light-emitting devices. In this case, the correctors 12d and 12dA each prepare table data for each of the light-emitting devices. Or, the correctors 12d and 12dA may each prepare single table data describing standard correction values, and also prepare information on individual difference for each of the light-emitting devices, so that the correctors 12d and 12dA may determine the correction values based on the table and the information.

(2-2) To determine the temperature of the light source 12a by estimation from the history of the activate current applied to the light source 12a, instead of using the temperature sensors 12c and 12i. More specifically, each of the correctors 12d and 12dA, or the light source controller 12bB accumulates the current values of the activate current in the memory at a regular time interval and generates history data. The correctors 12d and 12dA and the light source controller 12bB then each determine changes in the generated heat amount based on the history of the activate current read from the history data, and determine the temperature of the light source 12a while taking into account the amount of heat dissipated to the surroundings. At this time, a temperature sensor for detecting the ambient temperature of the light source 12a may be provided, so that the temperature determined by the corrector 12d or 12dA or the light source controller 12bB, or the maximum current value corrected based on this determined temperature may be corrected according to the ambient temperature detected by the temperature sensor. Also, if the activate current changes, a transient response for the change in temperature due to the changed activate current may be obtained from the thermal capacity of the light source 12a and its surrounding components, and the temperature at each time point may be determined by estimation based on the transient response characteristic.

(2-3) To set the maximum current value by the correctors 12d and 12dA, thus not by the light source controllers 12b, 12bA, and 12bB. In this case, the correctors 12d and 12dA each perform by themselves the processing of adding the correction value to the predetermined reference maximum value, to obtain the maximum current value. Or, the correctors 12d and 12dA each perform the processing which involves selecting the maximum current value corresponding to the detected temperature, from the table data describing reference maximum values in association with the respective temperatures.

(3) In the first, second, third, or fifth embodiment, the following modification is possible.

To provide the light source 12a in the central part 2, or in a separate light source apparatus. In this case, the optical fiber 11a, similarly to the signal cable 11d, extends to the central part 2 or the separate light source apparatus through or along the universal code 13.

(4) In the fourth embodiment, the following modification is possible.

To set the maximum output value based on power consumption of the light source 12a. In this modification, a maximum tolerable heat generation amount may be referred to, so that a value of the output light amount given at the power consumption that would produce this maximum tolerable heat generation amount is adopted as the maximum output value. In another option, a power amount available from the battery 12h may be referred to, so that an output light amount to be obtained when the light source is supplied with this available power amount is determined as the maximum output value.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system comprising:
a light source configured to emit light of a light amount corresponding to a magnitude of an activate current as a supply energy;
a temperature sensor configured to detect a temperature of the light source; and
a controller configured to:
adjust the magnitude of the activate current within a range less than or equal to a maximum supply value, to bring the light amount closer to a target value;
calculate, based on a proportional relationship between the activate current and an optical output of the light source when a predetermined reference temperature and an optical output of the light source are within an upper limit of the optical output of the light source, a correction value from a difference between a maximum activate current for the temperature of the light source detected by the temperature sensor and a maximum activate current for a predetermined reference temperature of the light source; and set the maximum supply value based on the maximum activate current for the predetermined reference temperature of the light source and the correction value.

2. The endoscope system according to claim 1, wherein the light source is configured to emit the light upon application of the activate current, and wherein the controller is configured to:

apply the activate current to the light source in a pulsed shape and in an intermittent manner to activate the light source;

control one or more conditions including a pulse width of the activate current, a pulse number of the activate current per unit time, a pulse density of the activate current per unit time, and a pulse amplitude of the activate current to change the light amount of the light; and limit the pulse amplitude to be the maximum supply value or lower.

3. The endoscope system according to claim 1, further comprising:

an optical converter configured to convert the light from the light source into illumination light, wherein the controller is configured to set, while referring to the temperature of the light source, the maximum supply value so that an intensity of the illumination light is equal to or below an upper limit predetermined according to a subject to be illuminated by the illumination light.

4. The endoscope system according to claim 1, wherein the controller is configured to set, while referring to the temperature of the light source, the maximum supply value so that an amount of heat generated by the light source is equal to or below a predetermined upper limit.

5. The endoscope system according to claim 1, wherein the controller is configured to set, while referring to the temperature of the light source, the maximum supply value so that power consumption by the light source is equal to or below a predetermined upper limit.

6. The endoscope system according to claim 1, wherein the controller is configured to adopt, as the maximum supply value, a magnitude of the activate current that yields a predetermined maximum optical output value for the light source at the temperature acquired by the temperature sensor or a magnitude of the activate current that yields a predetermined emission efficiency value for the light source, whichever is lower.

7. The endoscope system according to claim 1, further comprising a power source comprising the temperature sensor.

8. The endoscope system according to claim 7, wherein the power source is a battery.

9. The endoscope system according to claim 1, wherein the light source is configured to emit the light upon application of the activate current, and wherein the controller is configured to:

control the activate current applied to the light source to control the light source;

generate history data indicative of a history of activate currents applied to the light source; and determine the temperature of the light source based on the history data.

10. The endoscope system according to claim 1, further comprising a light sensor configured to detect the light amount output by the light source, wherein the controller is configured to set the maximum supply value according to a change in the light amount detected by the light sensor according to the temperature of the light source when the supply energy has a predetermined magnitude.

11. The endoscope system according to claim 10, wherein the light sensor is thermally insulated from the light source.

12. The endoscope system according to claim 1, wherein the controller is configured to:

set a minimum supply value based on the maximum supply value, and adjust the magnitude of the activate current to be equal to or above the minimum supply value for the light source to emit the light.

13. The endoscope system according to claim 1, wherein the light source is a laser diode.

14. The endoscope system according to claim 1, wherein the light source is a laser diode, and wherein the temperature sensor is configured to determine the temperature of the laser diode based on a change in an electrical characteristic of the laser diode.

15. The endoscope system according to claim 1, further comprising an optical converter configured to perform optical conversion of the light from the light source to obtain illumination light.

16. The endoscope system according to claim 15, wherein the optical converter is configured to convert a wavelength of the light from the light source.

* * * * *